US011472721B2

(12) United States Patent
McCague et al.

(10) Patent No.: US 11,472,721 B2
(45) Date of Patent: Oct. 18, 2022

(54) CHLORINE GENERATOR SYSTEM

(71) Applicant: Watkins Manufacturing Corporation, Vista, CA (US)

(72) Inventors: Michael McCague, Escondido, CA (US); Paul Oddou, Oceanside, CA (US)

(73) Assignee: Watkins Manufacturing Corporation, Vista, CA (US)

( * ) Notice: Subject to any disclaimer, the term of this patent is extended or adjusted under 35 U.S.C. 154(b) by 72 days.

(21) Appl. No.: 16/360,655

(22) Filed: Mar. 21, 2019

(65) Prior Publication Data

US 2019/0218116 A1 Jul. 18, 2019

Related U.S. Application Data

(62) Division of application No. 15/651,709, filed on Jul. 17, 2017.

(51) Int. Cl.
| | | |
|---|---|---|
| *C02F 1/467* | (2006.01) | |
| *A61L 2/26* | (2006.01) | |
| *A61L 2/18* | (2006.01) | |
| *C02F 1/461* | (2006.01) | |
| *C02F 103/42* | (2006.01) | |

(52) U.S. Cl.
CPC ............ *C02F 1/4674* (2013.01); *A61L 2/18* (2013.01); *A61L 2/26* (2013.01); *C02F 1/46109* (2013.01); *C02F 2103/42* (2013.01); *C02F 2201/006* (2013.01); *C02F 2201/4614* (2013.01)

(58) Field of Classification Search
None
See application file for complete search history.

(56) References Cited

U.S. PATENT DOCUMENTS

| | | | | |
|---|---|---|---|---|
| 2011/0010835 A1* | 1/2011 | McCague | ............. | C02F 1/4674 4/494 |
| 2012/0012209 A1* | 1/2012 | Andrews | ................ | E03B 7/074 137/599.15 |
| 2012/0181169 A1* | 7/2012 | Palmer | .................. | C02F 1/4674 204/275.1 |
| 2013/0105372 A1* | 5/2013 | Chen | ..................... | C02F 1/4674 210/94 |
| 2016/0376172 A1* | 12/2016 | Ellers | ...................... | C02F 1/463 204/672 |

OTHER PUBLICATIONS

Application No. 2019275609, IP Australia Examination Report, dated Apr. 16, 2020.
EPO 18836168.7 extended European search report, dated Jul. 17, 2020.
Application No. 2019275609, IP Australia Examination Report, dated Jul. 28, 2020.

(Continued)

*Primary Examiner* — Louis J Rufo
(74) *Attorney, Agent, or Firm* — Lapple Ubell IP Law, LLP; Franklin D. Ubell

(57) ABSTRACT

A chlorine generator apparatus wherein a housing is adapted to be mounted in an exterior, user-accessible surface of a spa and a chlorine generating electrode cartridge carrying a pair of electrodes is configured to be installable by a user in the housing and to thereafter be removeable by the user for replacement.

29 Claims, 11 Drawing Sheets

(56) References Cited

OTHER PUBLICATIONS

Application No. 759559, IP New Zealand Examination Report, dated Sep. 4, 2020.
EPO 18836168.7 Communication pursuant to Article 94(3) EPC, dated Feb. 23, 2021.
EPO 18836168.7 Communication pursuant to Article 94(3) EPC, dated Sep. 9, 2021.

* cited by examiner

CHLORINE GENERATOR SYSTEM

RELATED APPLICATIONS

This application is a divisional of, and claims the benefit of and priority to, U.S. patent application Ser. No. 15/651,709, filed Jul. 17, 2017, and entitled "Chlorine Generator System," which application is incorporated by reference herein in its entirety.

FIELD

The subject disclosure relates to chlorine generating systems and more particularly to a chlorine generator system for spas, tubs, pools and the like which features a disposable and consumer replaceable electrode cartridge.

DESCRIPTION OF RELATED ART

Various chlorine generating devices have been constructed in the past, for example, such as the drop-in chlorinator disclosed in U.S. Pat. No. 8,745,774, assigned to Watkins Manufacturing Corporation of Vista, Calif.

SUMMARY

Illustrative embodiments provide a chlorine generator installed in a spa and having a disposable and consumer replaceable electrode cartridge.

According to one embodiment, a chlorine generator apparatus comprises a housing adapted to be mounted in a user-accessible exterior surface of a spa and a chlorine generating electrode cartridge mounted in the housing and carrying first and second electrodes wherein the electrode cartridge is configured to be replaceable by a user.

According to another aspect of the disclosure, a housing is provided for receiving an electrode cartridge comprising a wall fitting mounted to a consumer-accessible surface of a spa and a cap removably attachable to the wall fitting by a user to provide user access to the electrode cartridge. In one embodiment, the housing may further comprise a lower housing section attached to a lower end of the wall fitting. The lower housing section may provide an electrode chamber wherein electrodes of the electrode cartridge may be disposed to generate chlorine for sanitizing the spa water.

According to another aspect, an electrode cartridge adapted to be installed into a housing by a user of a spa is provided comprising a handle component grippable by the user to insert the electrode cartridge into the housing and to pull the electrode cartridge out of the housing for replacement. In one embodiment, first and second electrodes are mounted beneath the handle for generating chlorine from spa water, and first and second electrical contacts are positioned to come into electrical contact with first and second electrical contacts located on an interior surface of the housing when the electrode cartridge is in an installed position in the housing.

According to another aspect, an electrode cartridge is provided comprising first and second electrodes each of which include a vertical portion which forms into a horizontal base portion from which extends an outwardly curved spring arm electrical contact. According to another aspect, the horizontal base portions of each of the first and second electrodes respectively fit into a respective mating opening in an electrode cup. In one embodiment, each horizontal base portion may be held in place by a bottom surface of a handle component of the electrode cartridge.

According to another aspect, a chlorine generator apparatus is provided wherein a housing comprises first and second internal electrical contact terminals formed on an inner surface thereof and wherein spring arm portions of the first and second electrodes of an electrode cartridge form electrical contact surfaces which are positioned to make electrical contact with the first and second internal electrical contact terminals when the electrode cartridge is fully inserted into the housing.

According to another aspect, a chlorine generator apparatus is provided comprising a groove formed in an inner wall of an electrode cartridge housing and first and second locking bars having first and second projections on respective outer ends thereof and mounted to slide laterally in an electrode cartridge such that the first and second projections can come into engagement with the groove in the housing inner wall in order to lock the electrode cartridge in position. A spring loaded plunger mounted in the electrode cartridge is shaped and positioned to cause the first and second locking bars to move laterally such that the first and second projections come into engagement with the groove.

DETAILED DESCRIPTION

Figure 1:
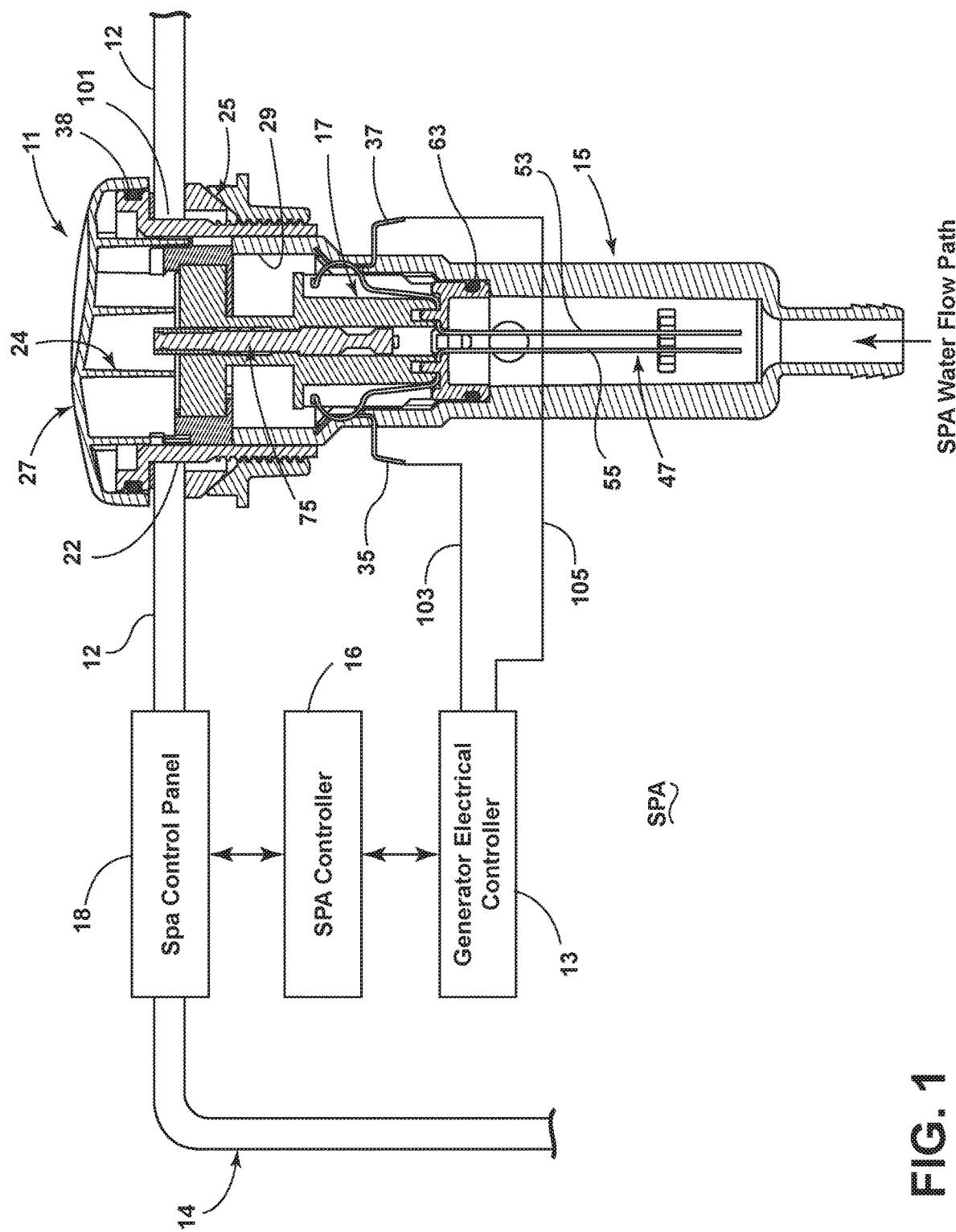
FIG. 1 is a schematic side view of a chlorine generator system according to an illustrative embodiment installed in a spa.
Figure 3:
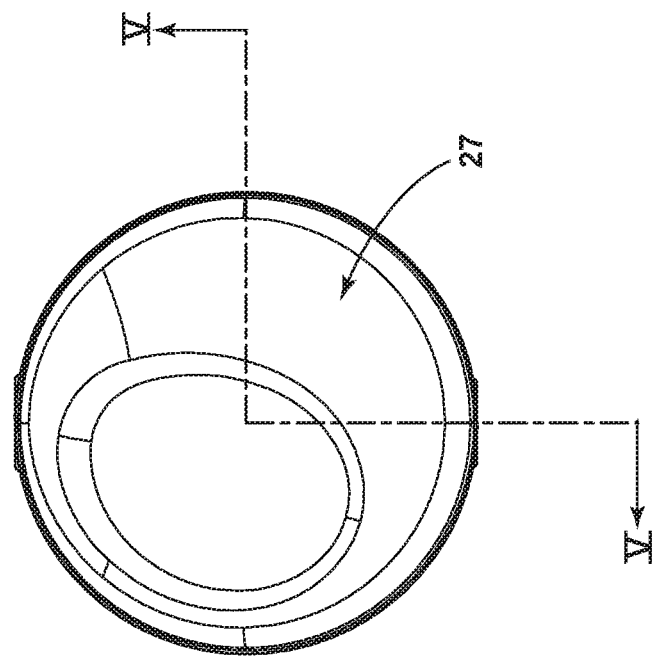
FIG. 3 is a top view of the chlorine generator of FIG. 2.
Figure 2:
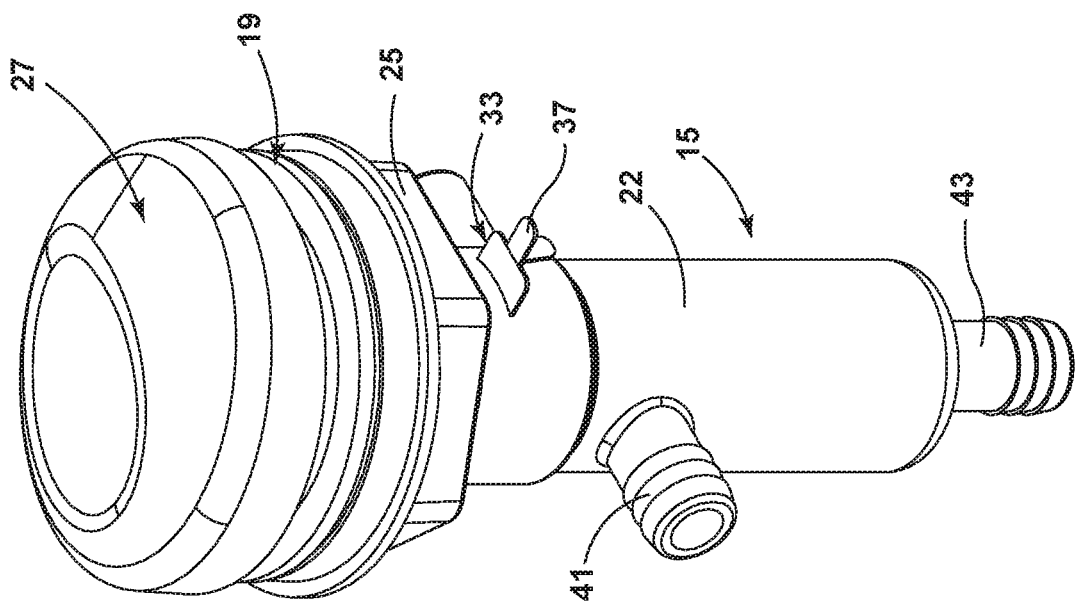
FIG. 2 is a perspective view of the chlorine generator employed in the system of FIG. 1.
Figure 4:
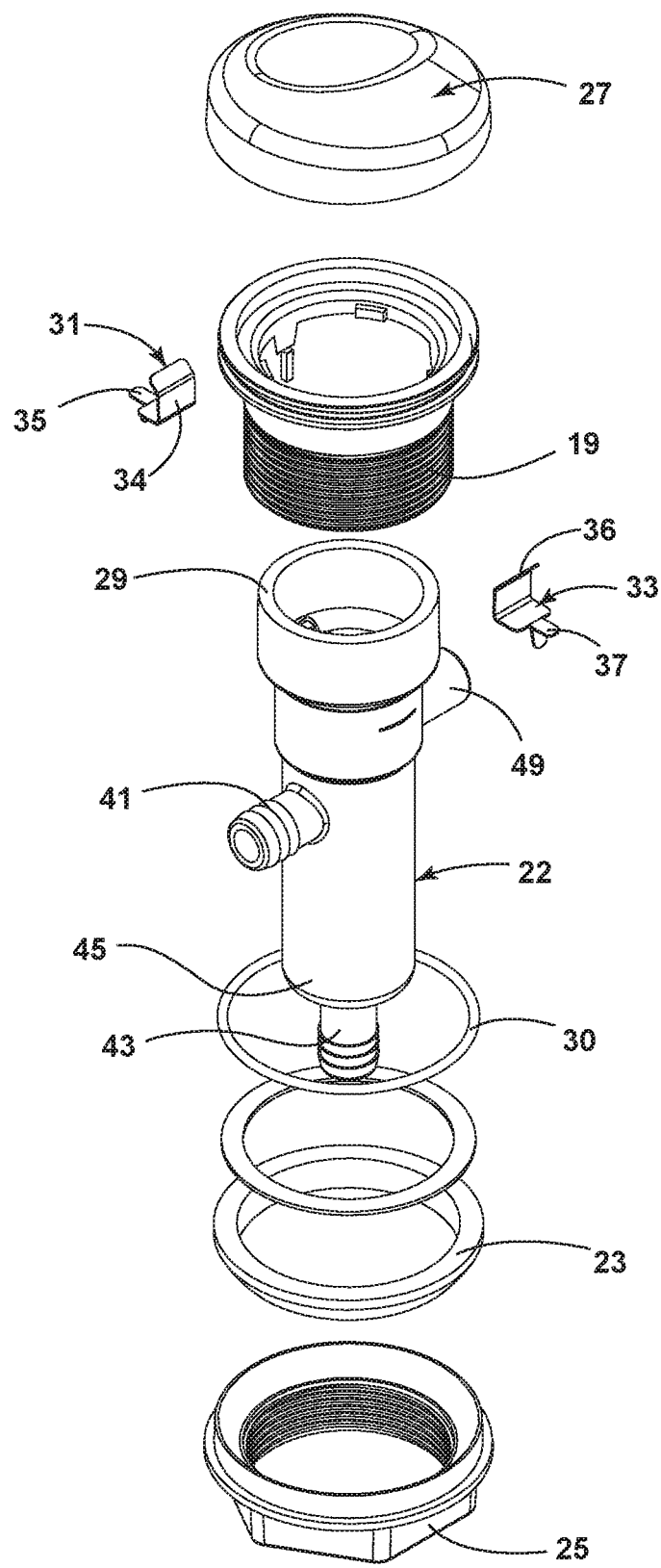
FIG. 4 is an exploded perspective view of the electrode housing of the chlorine generator of FIG. 2.
Figure 5:
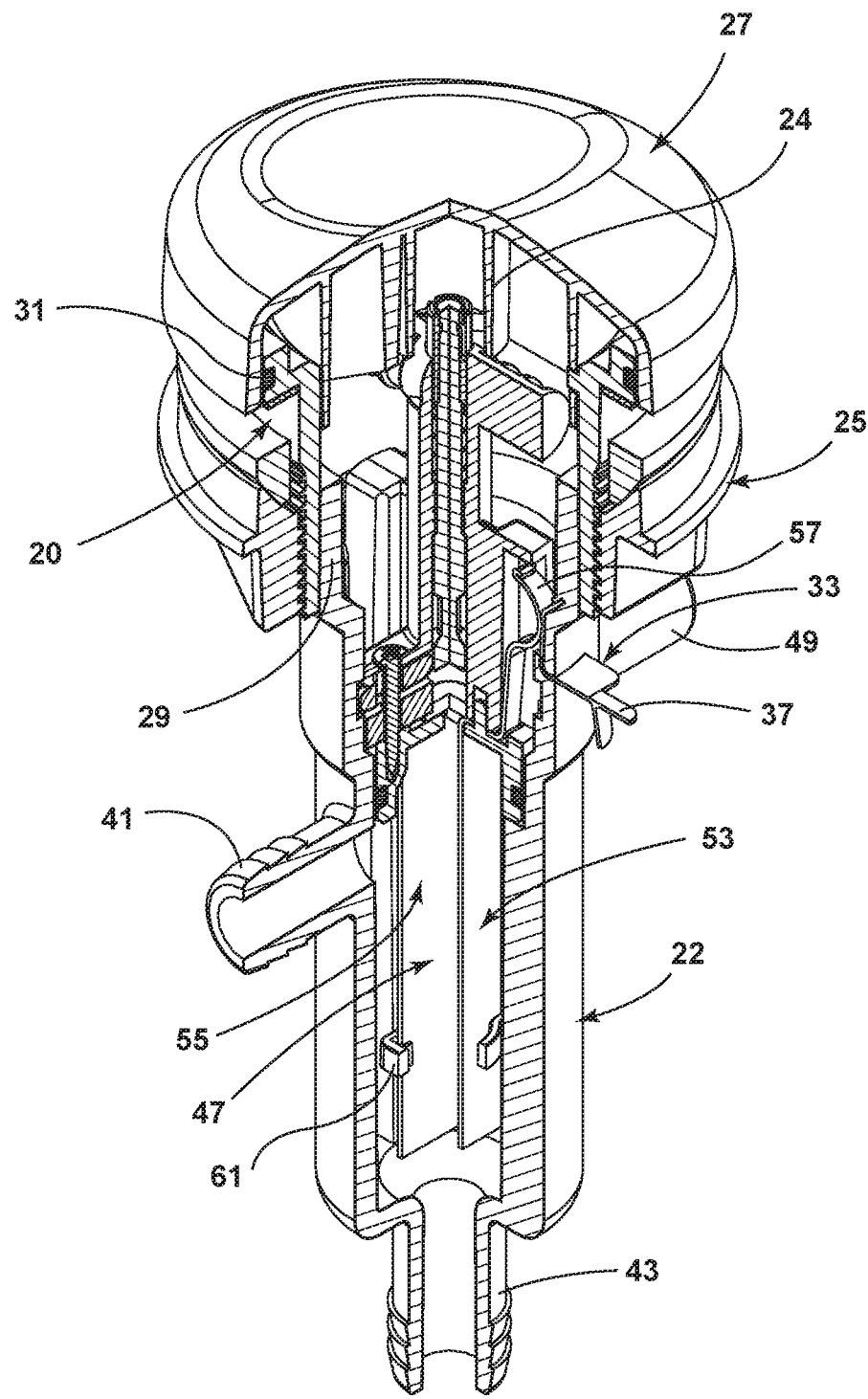
FIG. 5 is a sectional perspective view of the chlorine generator of FIG. 2 taken at V-V of FIG. 3.
Figure 7:
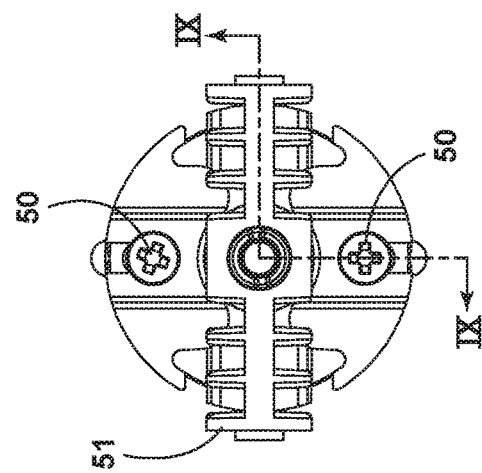
FIG. 7 is a top view of the electrode cartridge component of FIG. 6.
Figure 6:
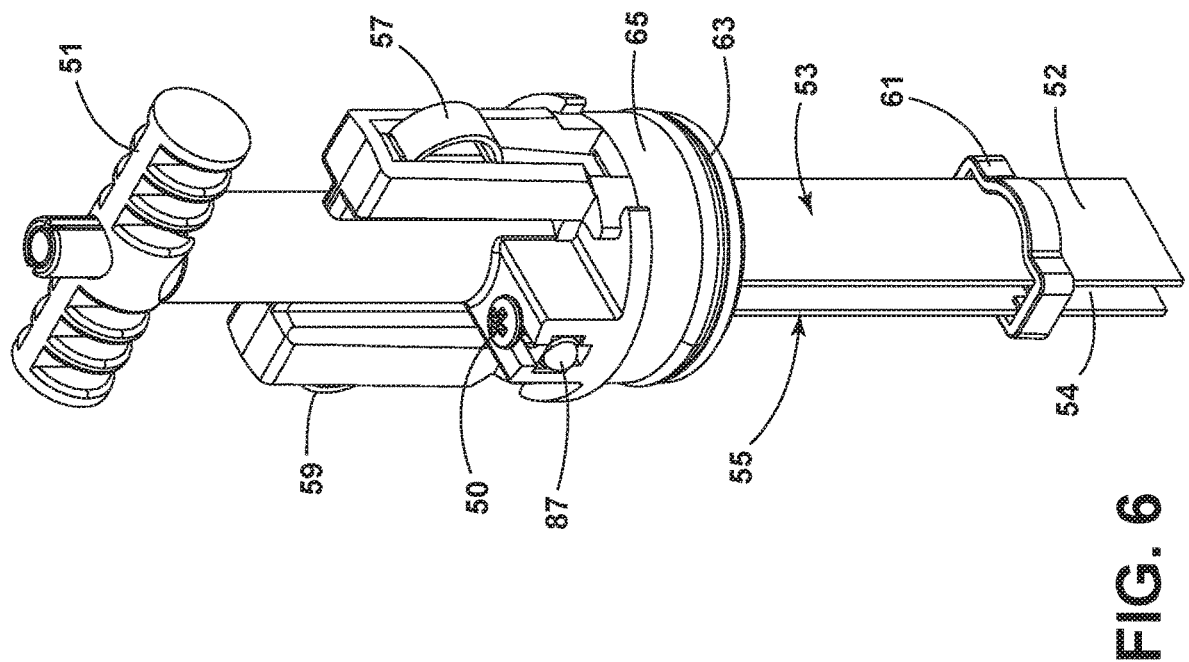
FIG. 6 is a perspective view of an electrode cartridge component of the chlorine generator of FIG. 2.

A chlorine generator system according to an illustrative embodiment is shown in FIG. 1. The illustrative system includes an electrical controller 13 and a chlorine generator 11 mounted in a bar top 12 of a spa 14. As may be appreciated, the bar top is an example of a user accessible surface of the spa where a user may be, for example, a user or owner of the spa 14. In one embodiment, the spa 14 may be a portable spa.

The chlorine generator 11 comprises an electrode cartridge housing 15 and an electrode cartridge 17. In the illustrative embodiment, the electrode cartridge 17 carries a pair of electrodes 53, 55, and is removably installed in the electrode cartridge housing 15. In one embodiment, the housing 15 is keyed to the electrode cartridge 17 to insure that the cartridge 17 may only be installed in the housing 15 in a proper manner. In an illustrative embodiment, water from the spa circulation path is routed up to the housing 15, through the electrodes 53, 55 and back out of the housing 15 to the spa 14.

In an illustrative embodiment, the electrical controller 13 controls generation of chlorine by the electrode cartridge 17. In one embodiment, the electrical controller 13 is relatively small in size, powered through the spa control system 16, and fully integrated into the spa 14. In one embodiment, the electrical controller 13 utilizes an RS485 communication protocol to transmit data and communicate with the spa control system 16. In one embodiment, the spa control system 16 may be accessed through and driven by a spa control panel 18. In another embodiment, a closed loop control system may be employed which includes a sensor which measures, for example, one or more of: chlorine, bromine, ozone, ORP, pH, conductivity, alkalinity, cyanuric acid, water hardness and/or temperature. The sensor then feeds parameters to an electronic controller which then automatically causes generation of the appropriate amount of chlorine via the chlorine generator 11.

In the illustrative embodiment, operation of the chlorine generator 11 is controlled by user settings for chlorine output made at the spa control panel 18. In an illustrative embodiment, the electrical controller 13 drives the electrodes of the chlorine generator 11 in a constant current mode to enable an optimal or desired chlorine generation rate. This mode of operation also allows the system to be driven at different specific current levels to control the generation rate of chlorine per hour depending on the user settings.

In one embodiment, the spa water is salted, for example, by adding sodium chloride to achieve a concentration of, for example, 2000 ppm. Such an embodiment may be characterized as a salt water chlorinator system.

As shown in FIGS. 2-5, in an illustrative embodiment, the electrode cartridge housing 15 comprises a wall fitting 19, which has circular groove 20, which receives an edge, e.g. 101 (FIG. 1), of the spa bar top 12. The wall fitting 19 mounts to the bar top 12 via a centering ring 23 and a nut 25. A cap 27 is screwed to the wall fitting 19 on the user side of the system to provide access to the electrode cartridge 17. An internal web portion 24 of the cap 27 also positions and holds the electrode cartridge 17 in place during operation.

In an illustrative embodiment, an upper portion 29 of a lower housing section 22 glues into or otherwise attaches to the wall fitting 19 to form a watertight attachment. An O-ring 30 mounts in a receptacle in the wall fitting 19 and provides a watertight seal between the wall fitting 19 and the cap 27. In illustrative embodiments, the wall fitting 19, cap 27, and lower housing section 22, may all be a suitable molded plastic material, such as, for example PVC or ABS plastic.

In the illustrative embodiment, the electrical connection of the electrode cartridge 17 to the controller 13 via electrical leads 103, 105 (FIG. 1) is completed through a pair of titanium electrical contacts 31, 33, which are molded into the housing 15 in watertight fashion. The contacts 31, 33 have flat vertical terminals 34, 36 adjacent an inside surface of the housing 15, as well as quick disconnect terminals 35, 37 on the outside of the housing 15. The electrical contacts 31, 33 thus enable dry electrical connections to the chlorine generator 11 and ease of service of the system.

Below the electrical contacts 31, 33 is a drain port 41. This port 41 allows for removal of any water that may have entered the dry portion of the housing 15 during removal and replacement of the electrode cartridge 17. A water inlet port 43 on the bottom 45 of the housing 15 allows spa water to enter the housing 15 and flow through the wet electrode chamber 47. At the top of the wet electrode chamber 47 is an outlet port 49 through which the chlorinated spa water flows into the spa 14. The vertical water flow through the housing 15 ensures efficient flushing of the housing 15 and removal of all liquids and gases generated in the housing 15 during operation of the chlorinator 11.

As shown in FIGS. 6-9, in an illustrative embodiment, the electrode cartridge 17 comprises a tee handle 51 and pair of mixed metal oxide titanium electrodes 53, 55. In illustrative embodiments, the electrodes 53, 55 may comprise, for example, titanium or niobium base metal with a suitable oxide coating, such as, for example, ruthenium oxide, iridium oxide, or platinum oxide. In other embodiments, the electrodes could be boron/nitrogen doped diamond.

In the illustrative embodiment, the electrodes 53, 55 are each formed as a single piece and each includes a respective rectangular vertical portion 52, 54, which forms into a respective horizontal base portion 56, 58, from which extends respective outwardly curved spring arm electrical contact 57, 59. The electrodes 53, 55 could of course be formed of multiple parts in other embodiments, for example, with separate wet electrode and spring contact components.

The horizontal base portions 56, 58 of each of the electrodes 53, 55 each fit into a respective mating opening 67, 69 in an electrode cup 65 and are held in place by a bottom surface 71 of the tee handle 51. An O-ring 63 provides a watertight seal between the housing 15 and the electrode cup 65.

First and second slots, e.g. 99, are defined in the electrode cup 65 on either side of horizontal projections 110, 111, through which a respective one of the electrodes 53, 54 are inserted. Potting material is applied to seal openings around the electrodes 53, 54. A cap 181 covers the opening in the electrode cup 65 and prevents potting material from leaking up through the opening. In an illustrative embodiment, the tee handle 51 and electrode cup 65 may be molded plastic components formed, for example, of PVC or ABS plastic.

In an illustrative embodiment, the design and shape of the electrodes 53, 55 provide a single piece component extending from the wetted electrode blade portions 52, 54 to the dry spring arm electrical contacts 57, 59. The wetted blade portions 52, 54 of the electrodes 53, 55 are equally spaced apart down the length of the cartridge 17, and a spacer 61 is mounted at the end of the cartridge 17 to ensure that the electrodes 53, 55 are held in proper position. The dry spring arm portions 57, 59 of the electrodes 53, 55 form electrical contact surfaces which are spring-biased into electrical contact with the flat vertical electrical contact terminals 34, 36, located on the interior of the electrode housing 15.

Figure 13:
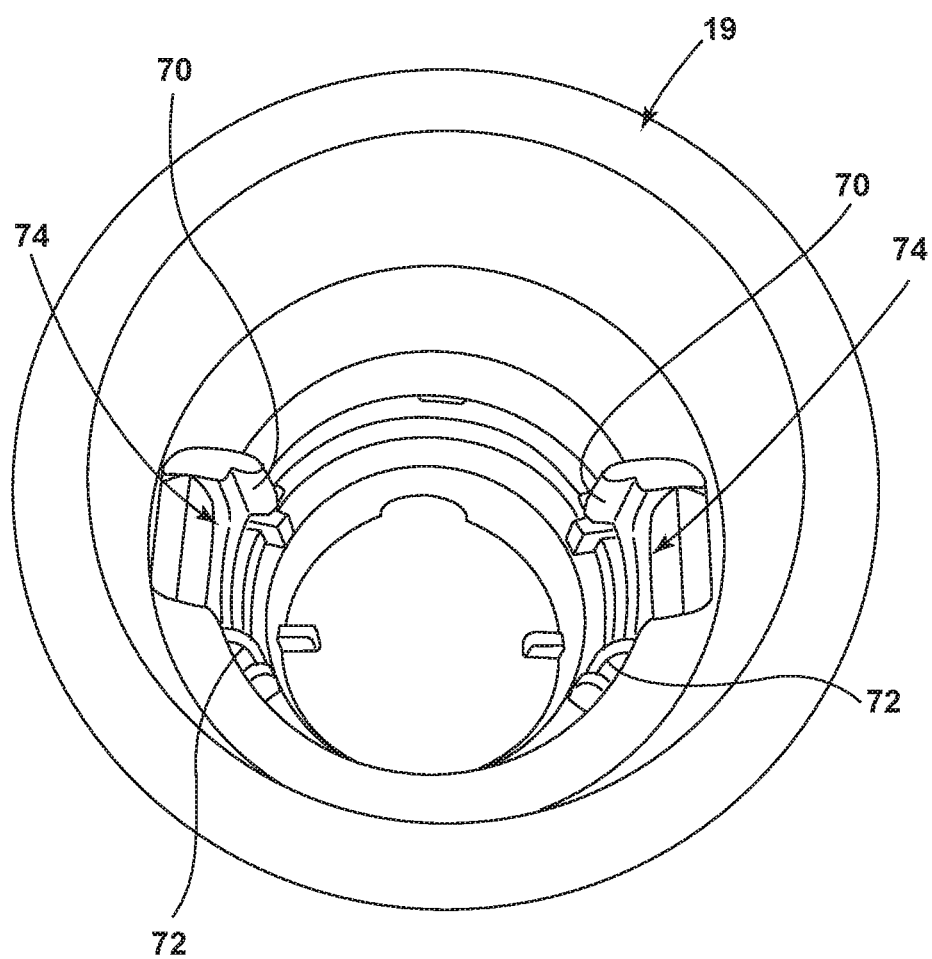
FIG. 13 is a perspective view of the open upper end of the electrode housing of FIG. 4.

As noted above, in one embodiment, the geometry of the electrode cartridge 17 permits installation of the electrode cartridge 17 into the housing 15 in only one direction and orientation, insuring proper electrical contact. In particular, in the illustrative embodiment, the outer vertical edges of the rectangular plastic guards, 60, 62 around each of the electrode contact arms 57, 59 extend outwardly and are shaped to mate with respective channels 74 defined by vertical guides 70, 72 formed on the inner wall of the electrode housing 19, as shown in FIG. 13. The electrode cartridge 17 is thereby keyed to the housing 19, permitting the cartridge 17 to be inserted in only one orientation.

Figure 8:
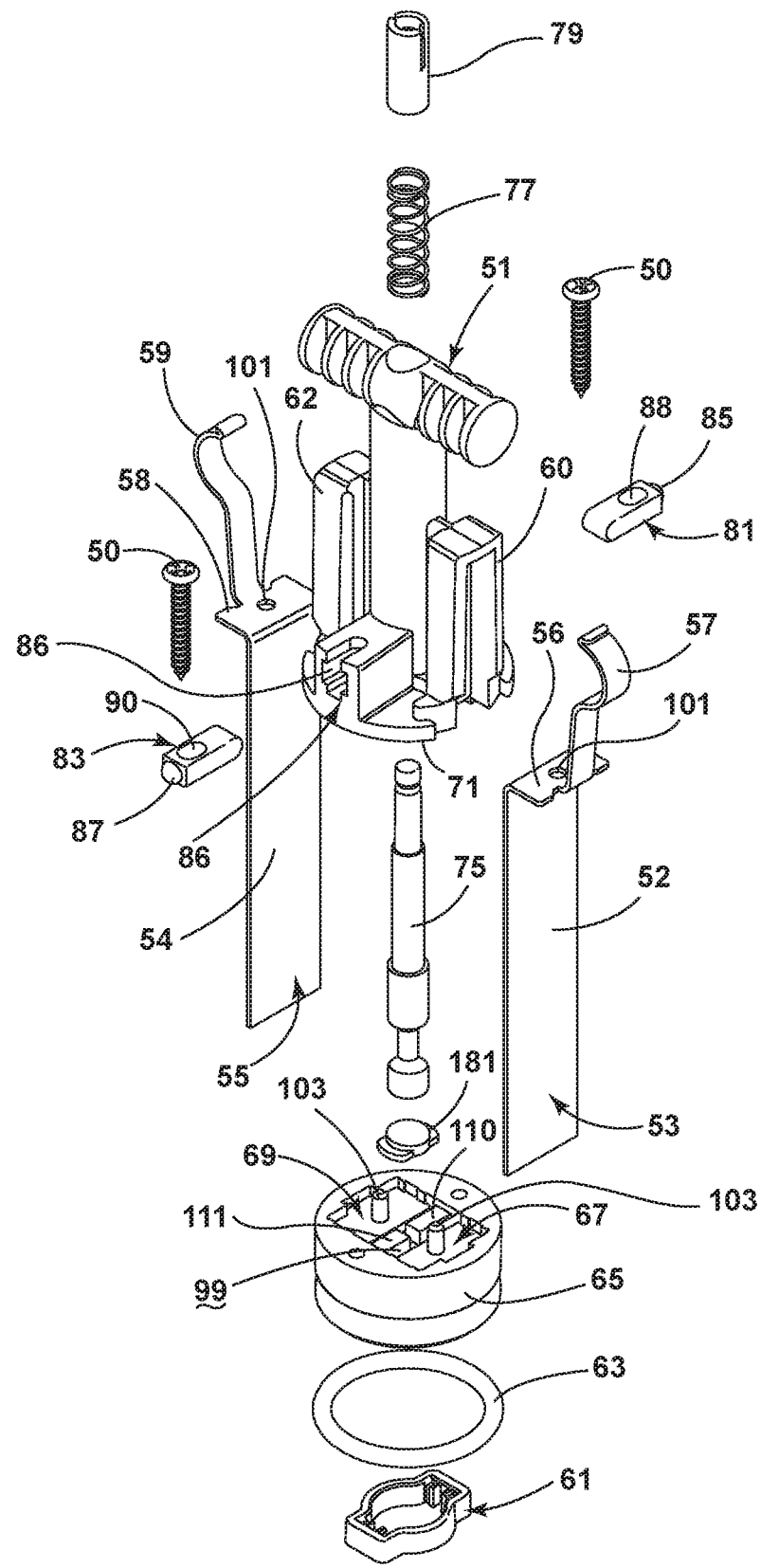
FIG. 8 is an exploded perspective view of the electrode cartridge component of FIG. 6.
Figure 9:
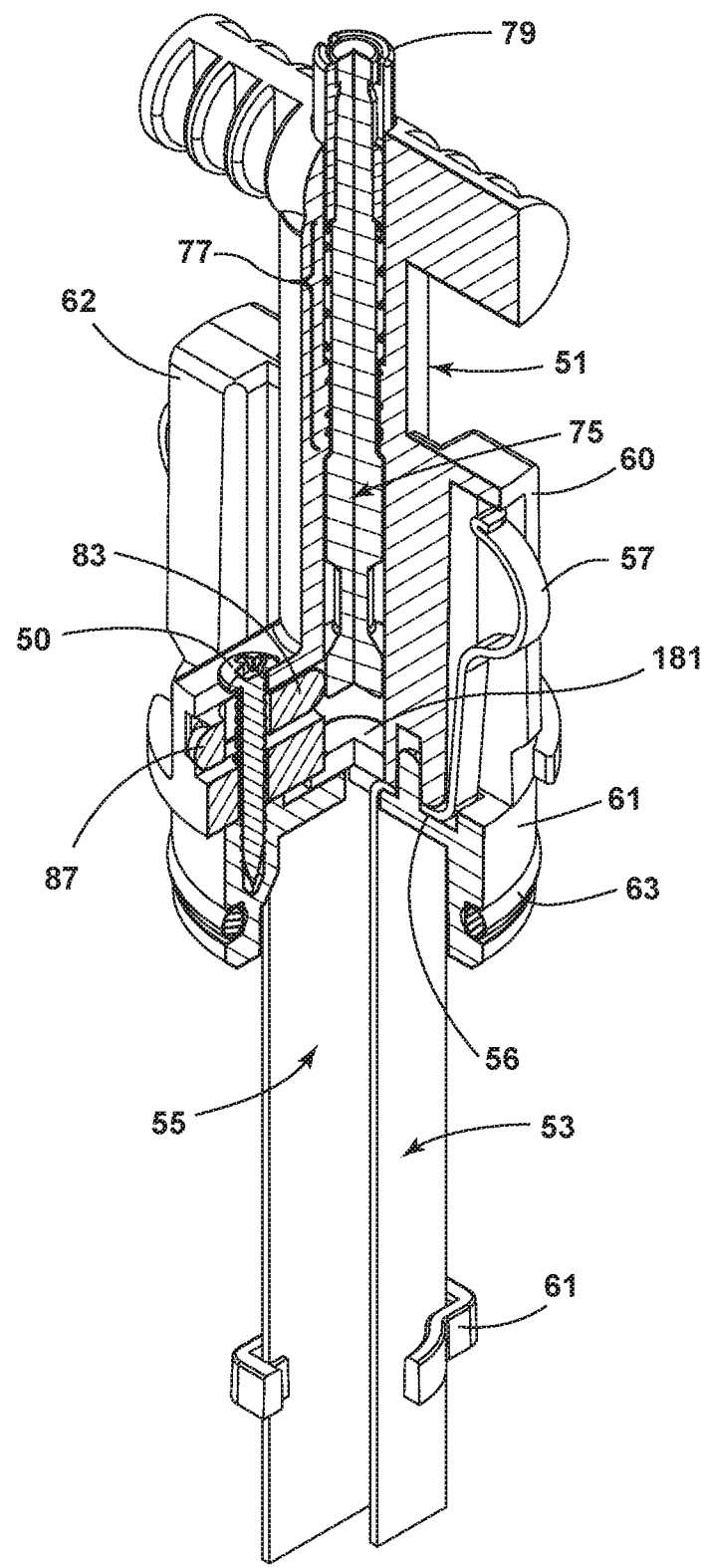
FIG. 9 is a perspective sectional view of the electrode cartridge component of FIG. 6 taken at IX-IX of FIG. 7.

In one illustrative embodiment, a locking mechanism is used to secure the cartridge 17 in place within the housing 15 independent of the cap 27. In particular, as shown in FIGS. 8 and 9, a spring loaded plunger is slidably mounted in an internal opening in the tee handle 51 and comprises a bottom shaft 75, a spring 77 and a plunger cap 79. Respective locking bars 81, 83 with ball-shaped end surfaces 85, 87 are positioned to move laterally in respective channels 86, 88 (FIG. 10) formed in the lower end of the tee handle 51. Oblong slots 88, 90, are formed in each of the locking bars 81, 83 to permit the locking bars 81, 83 to move laterally left and right with respect to the attachment screws 50, which attach the tee handle 51 to the electrode cup 65.

Figure 10:
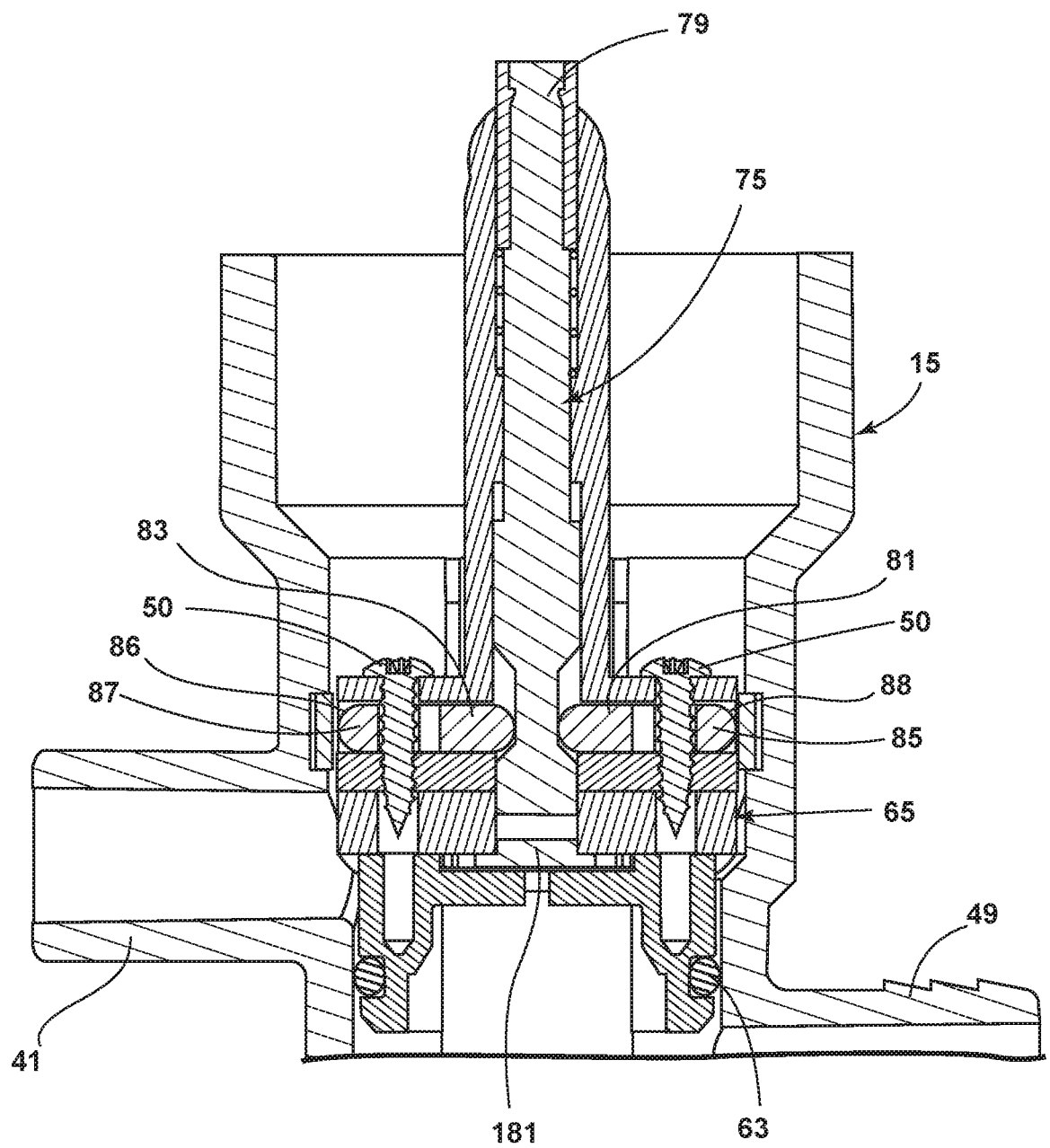
FIG. 10 is a sectional view illustrative of an electrode cartridge locking mechanism according to an illustrative embodiment in a first position.
Figure 11:
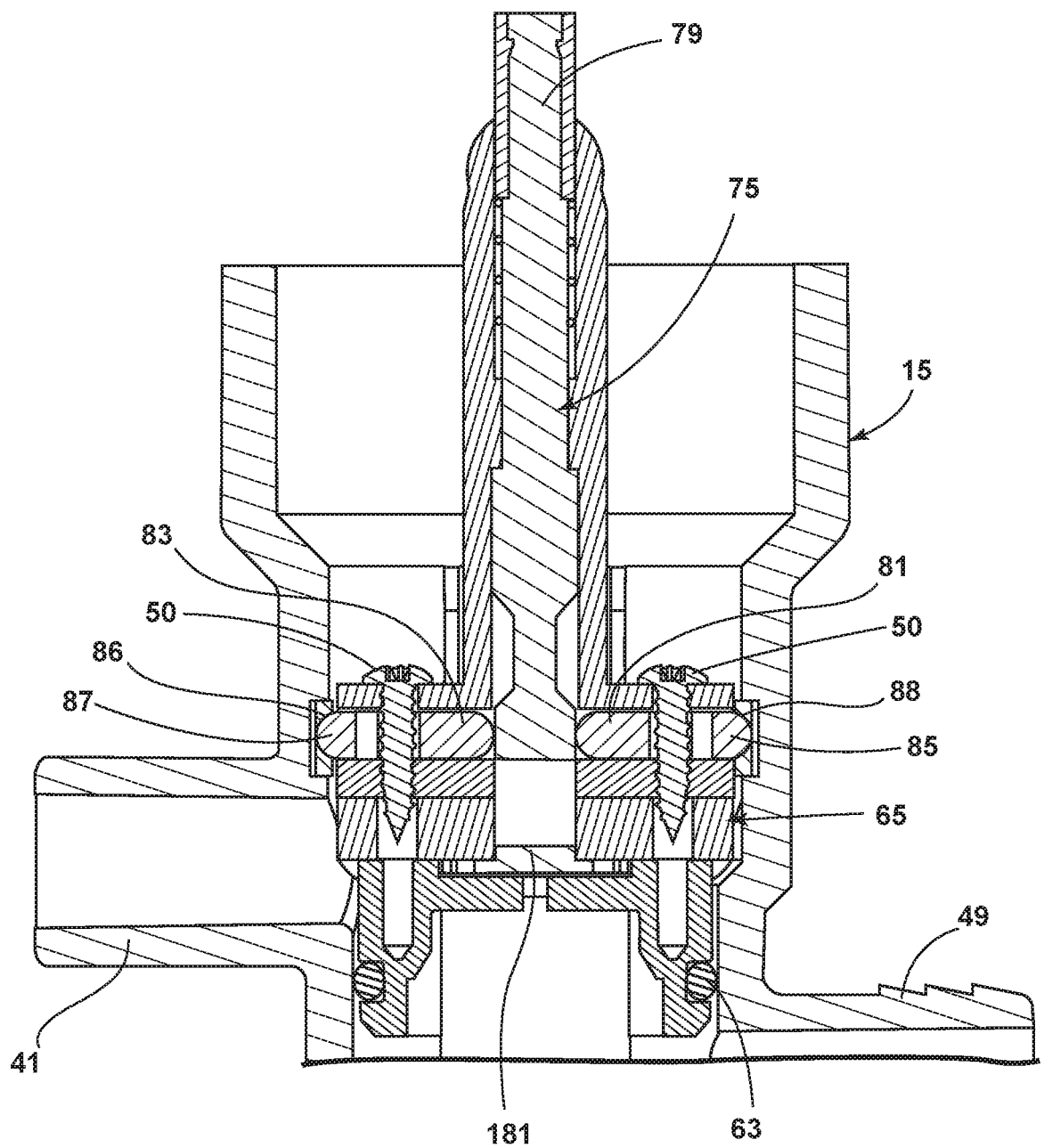
FIG. 11 is a sectional view of the illustrative electrode cartridge locking mechanism of FIG. 10 in a second position.
Figure 12:
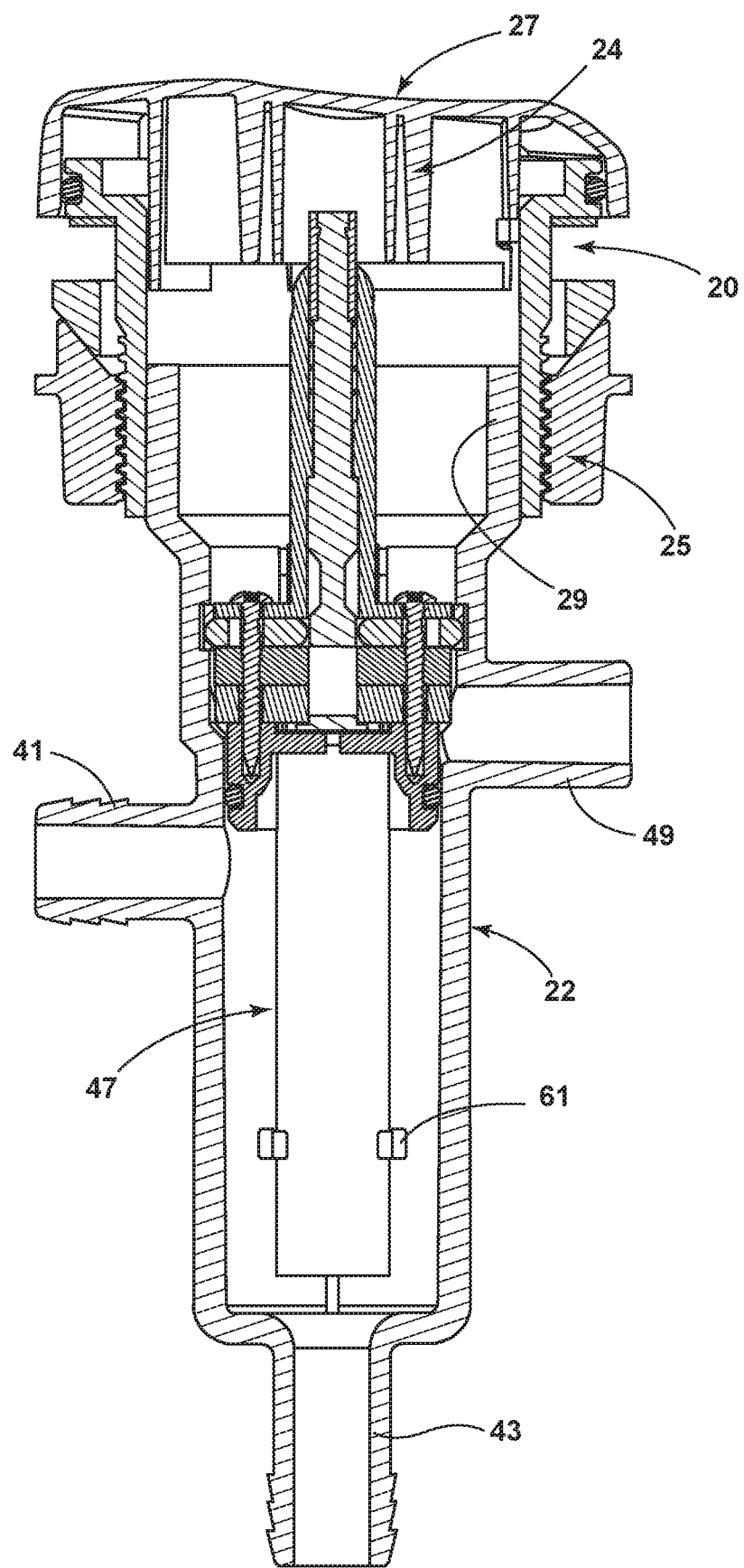
FIG. 12 is a sectional view of the chlorine generator of FIG. 2.

As a result of this construction, the cartridge 17 cannot be installed in the housing 15 without first pushing the plunger down by depressing the plunger cap 79 to retract the balls 85, 87 to a position within the respective channels 86, 88 in the lower end of the handle 51, as illustrated in FIG. 10. Once the balls 85, 87, are positioned adjacent the channel 90 in the housing 15, as shown in FIG. 10, the plunger can be pulled upward to the position shown in FIG. 11 so as to force lateral movement of the locking bars 81, 83, thereby causing the balls 85, 87 to enter the locking position shown in FIG. 11. If the cartridge 17 is not fully inserted into its proper position in the housing 15, the dimensioning of the cap 27 will cause the cap 27 to push the cartridge 17 into the locked position of FIG. 11 when the cap 27 is installed. If the cap 27 is thereafter removed, the cartridge 17 remains in its proper place.

To remove the cartridge 17, the tee handle 51 may be grasped with two fingers and the plunger cap 79 depressed with the thumb, thereby releasing the locking balls 85, 87 and allowing them to slide back. The cartridge 17 may then be lifted out of the housing 19.

Illustrative embodiments provide numerous advantages and improvements and in particular a low cost, disposable, consumer replaceable electrode cartridge, which is removable from the top side of a spa. Illustrative embodiments enable dry removal of the electrode cartridge, avoiding the risk of electrical shock. Spa-side control and operation of the system is also provided.

Significantly lower water maintenance requirements are also achieved by illustrative embodiments because the electrode cartridge is designed to last a short life and to be disposable. Hence, the necessity to control spa water parameters in order to maintain chlorine generator electrodes in operating condition is minimized or eliminated. For example, softening the spa water can help to minimize the need to clean the electrodes. The illustrative embodiments eliminate the need to clean the electrodes and hence the need to control spa water parameters in order to maintain the electrodes. Thus, when the electrode cartridge is spent (no longer operating in spec) the system instructs the owner to change it out.

From the foregoing, those skilled in the art will appreciate that various adaptations and modifications of the just described illustrative embodiments can be configured without departing from the scope and spirit of the invention. Therefore, it is to be understood that, within the scope of the appended claims, the invention may be practiced other than as specifically described herein.

What is claimed is:

1. A chlorine generator apparatus comprising:
  a housing structured and dimensioned to be mounted in and through an opening in an exterior, user-accessible surface of a spa and further structured and dimensioned such that when so mounted a portion of the housing resides in an interior area of the spa, said portion having an interior shaped to receive and enclose a disposable electrode cartridge unit;
  a disposable electrode cartridge unit constructed to generate chlorine and configured to be inserted by a spa user downwardly into said portion of the housing into an installed position where the cartridge is enclosed within the housing and to thereafter be removed from the housing as a unit and thrown away after use by the spa user and then replaced;
  wherein the housing has a first internal electrical contact mounted on an interior side surface thereof and a second internal electrical contact mounted on an interior side surface thereof and wherein the disposable electrode cartridge unit has first and second electrical contacts, each located on a side surface thereof; and
  wherein the first and second electrical contacts of the electrode cartridge unit are so positioned on the cartridge unit as to come into electrical contact with a respective one of said first and second internal electrical contacts mounted on an interior side surface of the housing as the disposable electrode cartridge unit is inserted into the installed position in the housing, thereby enabling electrical current flow to, and generation of chlorine by, the cartridge unit.

2. The chlorine generator apparatus of claim 1 wherein the housing further comprises a fluid inlet port and a fluid outlet port, the fluid inlet port and fluid outlet port being located on the portion of the housing structured and dimensioned to reside in said interior area.

3. The chlorine generator apparatus of claim 1 further comprising:
  a groove formed in an inner wall of said housing;
  first and second locking bars having first and second projections on respective outer ends thereof and mounted to slide laterally in said electrode cartridge unit such that said first and second projections can come into engagement with said groove to lock the electrode cartridge unit in position; and
  a spring loaded plunger shaped and positioned to cause said first and second locking bars to move laterally such that said projections come into engagement with said groove.

4. The chlorine generator apparatus of claim 1 wherein the disposable electrode cartridge unit comprises:
  first and second electrodes, each including a vertical portion which forms into a horizontal base portion from which extends an outwardly curved spring arm electrical contact.

5. The chlorine generator apparatus of claim 4 wherein the horizontal base portion of each of the first and second electrodes fits into a respective mating opening in an electrode cup, the electrode cup being configured to mount and position the first and second electrodes.

6. The chlorine generator apparatus of claim 5 wherein each horizontal base portion is held in place by a bottom surface of a handle component of the disposable electrode cartridge unit.

7. The chlorine generator apparatus of claim 1 wherein the first and second internal electrical contacts extend through the housing to provide respective electrical contact points external to the housing.

8. The chlorine generator apparatus of claim 1 wherein the electrode cartridge unit and housing are constructed such that electrical contact between the housing and the electrode cartridge unit is broken by the single step of pulling the electrode cartridge unit out of the housing.

9. The chlorine generator apparatus of claim 1 wherein the disposable electrode cartridge unit comprises a handle grippable by the spa user and first and second electrodes positioned to extend into said housing.

10. The chlorine generator apparatus of claim 1 further configured such that the disposable electrode cartridge unit is replaceable by an identical unused disposable electrode cartridge unit.

11. The chlorine generator apparatus of claim 1 wherein the electrode cartridge unit is configured to have first and second electrical contacts which respectively constitute the only respective entry and exit points for electrical current into and out of the electrode cartridge unit.

12. The chlorine generator apparatus of claim 11 wherein the electrode cartridge unit and housing are configured such that electrical contact between the housing and the electrode cartridge unit is broken by the single step of pulling the electrode cartridge unit out of the housing.

13. The chlorine generator apparatus of claim 1 wherein the electrode cartridge unit comprises a free standing unit wherein, as a free standing unit, first and second electrical contacts positioned on a side surface of the electrode cartridge unit constitute the only respective entry and exit points for electrical current into and out of the electrode cartridge unit.

14. The chlorine generator apparatus of claim 1 wherein the electrode cartridge unit is configured such that electrical current supplied to the electrode cartridge unit passes solely through first and second electrical contacts, each positioned on an exterior side surface of the electrode cartridge unit.

15. The chlorine generator apparatus of claim 1 wherein the disposable electrode cartridge unit is further configured such that no electrical wires enter or are attached to the disposable electrode cartridge unit when the disposable electrode cartridge unit is in an installed position in the housing.

16. The chlorine generator apparatus of claim 1 wherein each of the first and second electrical contacts of said electrode cartridge is further positioned (a) so as to be initially located above and out of electrical contact with the first and second electrical contacts located on the housing at the beginning of installation of the electrode cartridge into the housing, and (b) so as to thereafter come into electrical contact with a respective one of the first and second electrical contacts of the housing as the electrode cartridge is inserted downwardly into the housing and comes into an installed position in the housing.

17. The chlorine generator apparatus of claim 1 wherein the first and second electrical contacts of the housing and the first and second electrical contacts of the electrode cartridge are located beneath said exterior surface of the spa when the electrode cartridge is in an installed position in the housing.

18. A chlorine generator apparatus comprising:
a housing structured and dimensioned to be mounted in and through an opening in an exterior, user-accessible surface of a spa; and
an electrode cartridge configured to be installable by a user into said housing and to thereafter be removeable by the user and replaced;
wherein the electrode cartridge comprises a handle shaped to be grippable by the user to install the electrode cartridge into the housing and to pull the electrode cartridge out of the housing for replacement and first and second electrodes positioned to extend into said housing; and
wherein the housing comprises:
a wall fitting shaped to be installed into the opening in said exterior, user-accessible surface;
a cap removably attachable to the wall fitting by a user and configured to be removable from the wall fitting so as to provide the user access to reach through the wall fitting and manually grip the handle of the electrode cartridge when the cartridge is in an installed position in the housing;
wherein the housing has a first internal electrical contact mounted on an interior side surface thereof and a second internal electrical contact mounted on an interior side surface thereof and wherein the electrode cartridge has first and second electrical contacts, each located on a side surface thereof; and
wherein the first and second electrical contacts of the electrode cartridge are so positioned on the cartridge as to come into electrical contact with a respective one of said first and second internal electrical contacts mounted on an interior side surface of the housing as the electrode cartridge is inserted into the installed position in the housing, thereby enabling electrical current flow to, and generation of chlorine by, the cartridge unit.

19. The chlorine generator apparatus of claim 18 wherein the first and second internal electrical contacts extend through the housing to provide respective electrical contact points on an external surface of the housing.

20. The chlorine generator apparatus of claim 18 wherein the top surface of the spa is a bar top area of a portable spa.

21. A chlorine generator apparatus comprising:
a housing structured and dimensioned to be mounted into an opening in an exterior, user-accessible surface of a spa; and
a disposable electrode cartridge configured to be inserted by a user into an installed position in said housing and to thereafter be removed and thrown away after use by the user and then replaced; and
wherein the housing has a first internal electrical contact mounted on an interior side surface thereof and a second internal electrical contact mounted on an interior side surface thereof and wherein the disposable electrode cartridge has first and second electrical contacts, each located on a side surface thereof;
wherein the first and second electrical contacts of the electrode cartridge are positioned on the cartridge so as to be out of electrical contact with a respective one of said first and second internal electrical contacts of the housing when said disposable electrode cartridge is initially being inserted into the housing and to thereafter come into electrical contact with a respective one of said first and second internal electrical contacts as the electrode cartridge is inserted further into the housing; thereby enabling current flow through said electrode cartridge when said cartridge is in the installed position in said housing.

22. The chlorine generator apparatus of claim 21:
wherein the first and second electrical contacts located on the electrode cartridge respectively constitute the only respective entry and exit points for electrical current into and out of the electrode cartridge; and
wherein the electrode cartridge and housing are so constructed that electrical connection between the housing and the electrode cartridge is broken by the single step of pulling the electrode cartridge out of the housing.

23. The chlorine generator apparatus of claim 22 wherein the first and second electrical contacts of the housing and the first and second electrical contacts of the electrode cartridge are located beneath said exterior surface of the spa when the electrode cartridge is in an installed position in the housing.

24. The chlorine generator apparatus of claim 21 wherein the electrode cartridge and housing are so constructed that electrical connection between the housing and the electrode cartridge is broken by the single step of pulling the electrode cartridge out of the housing.

25. A chlorine generator apparatus comprising:
a housing structured and dimensioned to be mounted in and through an opening in an exterior, user-accessible surface of a spa, the housing having an interior and first and second internal electrical contacts, each mounted in the interior of the housing on an inner side surface of the housing and positioned to lie below said opening when the housing is installed in the spa; and
an electrode cartridge constructed and shaped to be installable by a spa user into the interior of said housing and to thereafter be removed from the housing and thrown away after use by the spa user and then replaced, the electrode cartridge comprising:
an electrode holder insertable into said housing and having a circular side surface;
first and second electrodes positioned to extend beneath said electrode holder and into said housing and further being constructed to generate chlorine to purify spa water;
sealing means located on said circular side surface and positioned to engage a side surface of said housing so as to define (a) a wet spa water containing portion of the housing and (b) a dry region located below said opening, above said sealing means, and between said electrode cartridge and the inner side surface of said housing when the electrode cartridge is in an installed position in the housing, the dry region being located above the wet spa water containing portion of the housing and mounting the first and second internal electrical contacts of the housing;
the electrode holder being further configured to position the first and second electrodes in spaced apart relation in the wet portion of the housing so as to create a flow path for electrical current between the first and second electrodes; and
first and second electrical contacts, each located on a side surface of said electrode cartridge and each positioned to be located in said dry region opposite to and in contact with a respective one of the first and second internal electrical contacts mounted in the dry region when the electrode cartridge is in the installed position in the interior of the housing.

26. The chlorine generator apparatus of claim 25 wherein said sealing means comprises an O-ring.

27. The chlorine generator apparatus of claim 25 wherein each of the first and second electrical contacts located on a side surface of said electrode cartridge is further positioned (a) so as to be initially located above and out of electrical contact with the first and second internal electrical contacts located on an inner side surface of the housing at the beginning of installation of the electrode cartridge into the housing, and (b) so as to thereafter come into electrical contact with a respective one of the first and second internal electrical contacts of the housing as the electrode cartridge is inserted downwardly into the housing and comes into an installed position in the housing.

28. The chlorine generator apparatus of claim 25 wherein the electrode cartridge and housing are so constructed that electrical connection between the housing and the electrode cartridge is broken by the single step of pulling the electrode cartridge out of the housing.

29. The chlorine generator apparatus of claim 25 further comprising a handle shaped to be grippable by the user of the spa to insert the electrode cartridge into the housing and to pull the electrode cartridge out of the housing for replacement.

* * * * *